United States Patent
Rao-Naik et al.

(10) Patent No.: US 10,676,773 B2
(45) Date of Patent: Jun. 9, 2020

(54) ANTIBODIES CONJUGATABLE BY TRANSGLUTAMINASE AND CONJUGATES MADE THEREFROM

(71) Applicant: BRISTOL-MYERS SQUIBB COMPANY, Princeton, NJ (US)

(72) Inventors: Chetana Rao-Naik, Walnut Creek, CA (US); Shrikant Deshpande, Fremont, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 107 days.

(21) Appl. No.: 15/555,594

(22) PCT Filed: Mar. 1, 2016

(86) PCT No.: PCT/US2016/020192
§ 371 (c)(1),
(2) Date: Sep. 5, 2017

(87) PCT Pub. No.: WO2016/144608
PCT Pub. Date: Sep. 15, 2016

(65) Prior Publication Data
US 2018/0037921 A1    Feb. 8, 2018

Related U.S. Application Data

(60) Provisional application No. 62/130,673, filed on Mar. 10, 2015.

(51) Int. Cl.
*C12P 21/02* (2006.01)
*A61K 47/68* (2017.01)
*C07K 16/28* (2006.01)
*C07K 16/30* (2006.01)

(52) U.S. Cl.
CPC .......... *C12P 21/02* (2013.01); *A61K 47/6803* (2017.08); *A61K 47/6811* (2017.08); *A61K 47/6849* (2017.08); *A61K 47/6851* (2017.08); *A61K 47/6889* (2017.08); *C07K 16/28* (2013.01); *C07K 16/30* (2013.01); *C12Y 203/02013* (2013.01); *C07K 16/2875* (2013.01); *C07K 2317/51* (2013.01); *C07K 2317/52* (2013.01)

(58) Field of Classification Search
CPC ............ A61K 47/6889; A61K 47/6803; C12Y 203/02013
See application file for complete search history.

(56) References Cited

U.S. PATENT DOCUMENTS

| | | | |
|---|---|---|---|
| 6,322,996 B1 | 11/2001 | Sato et al. | |
| 8,268,970 B2 | 9/2012 | Terrett et al. | |
| 8,852,599 B2 | 10/2014 | Zhang et al. | |
| 8,865,875 B2 | 10/2014 | Liu et al. | |
| 2005/0136491 A1 | 6/2005 | Chen et al. | |
| 2007/0184537 A1 | 8/2007 | Schibli et al. | |
| 2010/0150950 A1 | 6/2010 | Coccia et al. | |
| 2011/0184147 A1 | 7/2011 | Kamiya et al. | |
| 2013/0189287 A1 | 7/2013 | Bregeon et al. | |
| 2013/0224228 A1* | 8/2013 | Jackson ........... A61K 39/39558 424/179.1 |
| 2013/0230543 A1 | 9/2013 | Pons et al. | |

FOREIGN PATENT DOCUMENTS

| | | | |
|---|---|---|---|
| WO | WO-03068821 A2 * | 8/2003 | ......... C07K 16/2803 |
| WO | WO 2014/072482 A1 | 5/2014 | |
| WO | WO 2014/202773 A1 | 12/2014 | |
| WO | WO 2014/202775 A1 | 12/2014 | |

OTHER PUBLICATIONS

Farias et al (Bioconjugate Chemistry, 2014, vol. 25, pp. 240-250) (Year: 2014).*
Ryan et al (British Journal of Cancer, 2010, vol. 103, pp. 676-684) (Year: 2010).*
Chari et al (Angewandte Chemie, 2014, vol. 53, pp. 3796-3827) (Year: 2014).*
Golfier et al (Molecular Cancer Therapeutics, 2014, vol. 13, pp. 1537-1548) (Year: 2014).*
Bruckdorfer et al (Current Pharmaceutical Biotechnology, 2004, vol. 5, pp. 29-43) (Year: 2004).*
Dennier, et al., "Transglutaminase-Based Chemo-Enzymatic Conjugation Approach Yields Homogeneous Antibody-Drug Conjugates," *Bioconjugate Chemistry*, vol. 25, pp. 569-578, 2014.
Fontana, et al., "Site-Specific Modification and PEGylation of Pharmaceutical Proteins Mediated by Transglutaminase" *Advanced Drug Delivery Reviews*, No. 60, pp. 13-28, 2008.
Innate Pharma, "A New Site Specific antibody Conjugation Using Bacterial Transglutaminase," *ADC Summit*, pp. 1-29, Oct. 15, 2013.
Jeger et al., "Site-Specific and Stoichiometric Modification of Antibodies by Bacterial Transglutaminase," *Angew. Chem. Int. Ed.* 49, pp. 9995-9997, 2010.
Lin, et al., "Transglutaminase-Catalyzed Site-Specific Conjugation of Small-Molecule Probes to Proteins in Vitro and on the Surface of Living Cells," *J. Am. Chem. Soc.*, vol. 128, pp. 4542-4543, 2006.
Mero, et al., "Transglutaminase-Mediated PEGylation of Proteins: Direct Identification of the Sites of Protein Modification by Mass Spectrometry Using a Novel Monodisperse PEG," *Bioconjugate Chem.*, vol. 20, pp. 384-389, 2009.

(Continued)

*Primary Examiner* — Karen A. Canella
(74) *Attorney, Agent, or Firm* — Yuan Chao

(57) ABSTRACT

An antibody has at a heavy chain thereof a C-terminal extension that includes at least one glutamine that is a substrate for transglutaminase, enabling the transglutaminase-mediated preparation antibody-drug conjugates using such antibody.

Figure 1A:
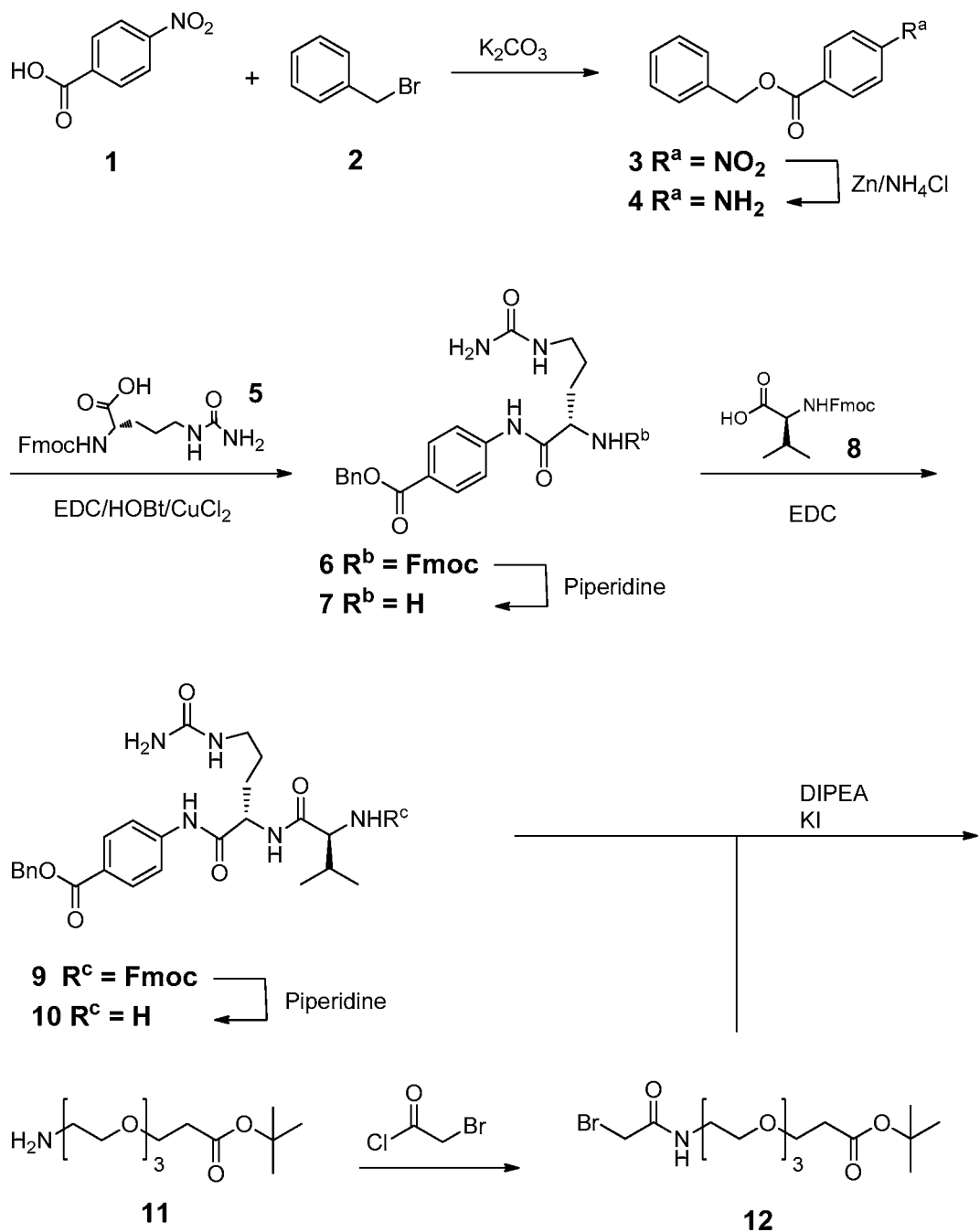

6 Claims, 6 Drawing Sheets
Specification includes a Sequence Listing.

(56) References Cited

OTHER PUBLICATIONS

Mindt, et al., "Modification of Different IgG1 Antibodies via Glutamine and Lysine Using Bacterial and Human Tissue Transglutaminase," *Bioconjugate Chem*, vol. 19, pp. 272-278, 2008.
Sato, Haruya, "Enzymatic Procedure for Site-Specific Pegylation of Proteins" *Advanced Drug Delivery Review*, No. 54, pp. 487-504, 2002.
Schrama, et al., "Antibody Targeted Drugs as Cancer Therapeutics," *Nature Reviews Drug Discovery*, vol. 5, pp. 147-159, 2006.
Strop, et al., "Location Matters: Site of Conjugation Modulates Stability and Pharmacokinetics of Antibody Drug Conjugates," *Chemistry & Biology*, vol. 20, pp. 161-167, 2013.
Sugimura, et al., "Novel Site-Specific Immobilization of a Functional Protein Using a Preferred Substrate Sequence for Transglutaminase 2," *Journal of Biotechnology*, vol. 131, pp. 121-127, 2007.

* cited by examiner

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: C-Term EEQYASTY

<400> SEQUENCE: 1

Glu Glu Gln Tyr Ala Ser Thr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: C-Term EEQYQSTY

<400> SEQUENCE: 2

Glu Glu Gln Tyr Gln Ser Thr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: C-Term EEQYNSTY

<400> SEQUENCE: 3

Glu Glu Gln Tyr Asn Ser Thr Tyr
1               5

<210> SEQ ID NO 4
```

```
<211> LENGTH: 330
<212> TYPE: PRT
<213> ORGANISM: Artificial Sequence
<220> FEATURE:
<223> OTHER INFORMATION: IgG1 Variant
<220> FEATURE:
<221> NAME/KEY: MISC_FEATURE
<222> LOCATION: (330)..(330)
<223> OTHER INFORMATION: Presence optional

<400> SEQUENCE: 4
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 5
<211> LENGTH: 1020
<212> TYPE: DNA
```

<213> ORGANISM: Artificial Sequence
<220> FEATURE:
<223> OTHER INFORMATION: HC with EEQYASTY C-Term
<220> FEATURE:
<221> NAME/KEY: CDS
<222> LOCATION: (1)..(1020)

<400> SEQUENCE: 5

```
gct agc acc aag ggc cca tcg gtc ttc ccc ctg gca ccc tcc tcc aag         48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac         96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc        144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc        192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc        240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag        288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc        336
Arg Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca        384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc        432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg        480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag        528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg        576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac        624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg        672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag        720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat        768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
```

```
                    275                 280                 285
ctc tat agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tcc ccg ggt aaa gag gag cag tac gcg agc     1008
Gln Lys Ser Leu Ser Leu Ser Pro Gly Lys Glu Glu Gln Tyr Ala Ser
                325                 330                 335 acg tac cgt tag                                                     1020
Thr Tyr Arg <210> SEQ ID NO 6
<211> LENGTH: 339
<212> TYPE: PRT
<213> ORGANISM: Artificial Sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Glu Glu Gln Tyr Ala Ser
                325                 330                 335

Thr Tyr Arg

<210> SEQ ID NO 7
<211> LENGTH: 1020
<212> TYPE: DNA
<213> ORGANISM: Artificial Sequence
<220> FEATURE:
<223> OTHER INFORMATION: HC with EEQYQSTY C-Term
<220> FEATURE:
<221> NAME/KEY: CDS
<222> LOCATION: (1)..(1020)

<400> SEQUENCE: 7 gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
                20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
            35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
        50                  55                  60 ctc agc agc gtg gtg acc gtg ccc tcc agc agc ttg ggc acc cag acc     240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag     288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc     336
Arg Val Glu Pro Lys Ser Cys Asp Lys Thr His Thr Cys Pro Pro Cys
                100                 105                 110 cca gca cct gaa ctc ctg ggg gga ccg tca gtc ttc ctc ttc ccc cca     384
Pro Ala Pro Glu Leu Leu Gly Gly Pro Ser Val Phe Leu Phe Pro Pro
            115                 120                 125 aaa ccc aag gac acc ctc atg atc tcc cgg acc cct gag gtc aca tgc     432
Lys Pro Lys Asp Thr Leu Met Ile Ser Arg Thr Pro Glu Val Thr Cys
        130                 135                 140 gtg gtg gtg gac gtg agc cac gaa gac cct gag gtc aag ttc aac tgg     480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag     528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg     576
Glu Gln Tyr Asn Ser Thr Tyr Arg Val Val Ser Val Leu Thr Val Leu
                180                 185                 190 cac cag gac tgg ctg aat ggc aag gag tac aag tgc aag gtc tcc aac     624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg     672
```

```
Lys Ala Leu Pro Ala Pro Ile Glu Lys Thr Ile Ser Lys Ala Lys Gly
            210                 215                 220 cag ccc cga gaa cca cag gtg tac acc ctg ccc cca tcc cgg gag gag        720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat        768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac        816
Pro Ser Asp Ile Ala Val Glu Trp Glu Ser Asn Gly Gln Pro Glu Asn
            260                 265                 270 aac tac aag acc acg cct ccc gtg ctg gac tcc gac ggc tcc ttc ttc        864
Asn Tyr Lys Thr Thr Pro Pro Val Leu Asp Ser Asp Gly Ser Phe Phe
        275                 280                 285 ctc tat agc aag ctc acc gtg gac aag agc agg tgg cag cag ggg aac        912
Leu Tyr Ser Lys Leu Thr Val Asp Lys Ser Arg Trp Gln Gln Gly Asn
290                 295                 300 gtc ttc tca tgc tcc gtg atg cat gag gct ctg cac aac cac tac acg        960
Val Phe Ser Cys Ser Val Met His Glu Ala Leu His Asn His Tyr Thr
305                 310                 315                 320 cag aag agc ctc tcc ctg tcc ccg ggt aaa gag gag cag tac cag agc       1008
Gln Lys Ser Leu Ser Leu Ser Pro Gly Lys Glu Glu Gln Tyr Gln Ser
                325                 330                 335 acg tac cgt tag                                                       1020
Thr Tyr Arg <210> SEQ ID NO 8
<211> LENGTH: 339
<212> TYPE: PRT
<213> ORGANISM: Artificial Sequence
<220> FEATURE:
<223> OTHER INFORMATION: Synthetic Construct

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Glu Glu Gln Tyr Gln Ser
                325                 330                 335

Thr Tyr Arg
```

ANTIBODIES CONJUGATABLE BY TRANSGLUTAMINASE AND CONJUGATES MADE THEREFROM

TECHNICAL FIELD

This invention relates to antibodies modified so that they are conjugatable to drug moiety by the enzyme transglutaminase, and conjugates made from such antibodies.

BACKGROUND OF THE INVENTION

A type of anticancer agent that has attracted intense current interest is an antibody-drug conjugate (ADC), also known as an immunoconjugate. In an ADC, a therapeutic agent (drug) is covalently linked to an antibody whose antigen is expressed by a cancer cell. The antibody, through its binding to the antigen, serves to deliver the ADC to the cancer. Once there, cleavage of the covalent link or degradation of the antibody results in the release of the therapeutic agent at the cancer site. Conversely, while the ADC is circulating in the blood system, the therapeutic agent is held inactive because of its covalent linkage to the antibody. Thus, the therapeutic agent in an ADC can be much more potent (i.e., cytotoxic) than ordinary chemotherapy agents because of its localized release. Thus, an ADC comprises three components: (1) the antibody, (2) a drug, and (3) a linker covalently joining the antibody and the drug. For a review on ADCs, see Schrama et al. 2006.

A key step in the preparation of an ADC is the covalent joining step, also referred to as the conjugation step. Many methods having been disclosed for effecting conjugation. One that has engendered substantial recent interest is conjugation mediated by transglutaminase (TGase), in particular bacterial transglutaminase (BTG). See, for example, Jeger et al. 2010.

BTG forms an amide bond between the carboxamide side chain of a glutamine (the amine acceptor) and the ε-amino group of a lysine (the amine donor). Specificity-wise, transglutaminase is selective regarding the glutamine residue, e.g. requiring that it be located in a flexible part of a protein loop and flanked by particular amino acids, but is promiscuous regarding the lysine residue, for example readily accepting the amino group of an alkyleneamino compound as a lysine ε-amino surrogate. See Fontana et al. 2008.

In a typical BTG-mediated conjugation the glutamine residue is located on the antibody, while the amino group is located on the linker-drug moiety, as shown below:

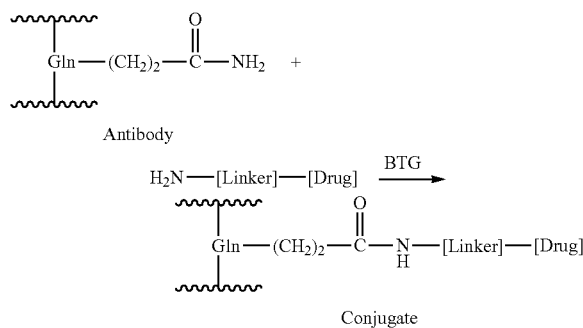

In this scheme, the antibody acts as an amine acceptor and the H$_2$N-[Linker]-[Drug] moiety acts as an amine donor.

The location of a glutamine residue on a polypeptide chain has a large effect on its susceptibility to BTG mediated transamidation. None of the glutamine residues on an antibody are normally BTG substrates and some modification of the antibody is necessary to induce BTG susceptibility. Typically, an antibody is glycosylated at asparagine 297 (N297) of the heavy chain (N-linked glycosylation). Jeger et al. 2010 discovered that deglycosylation of the antibody, either by eliminating the glycosylation site through an N297A substitution or post-translation enzymatic deglycosylation, renders nearby glutamine 295 (Q295) BTG-susceptible. They also showed that an N297Q substitution not only eliminates glycosylation, but also introduces a second glutamine residue (at position 297) that too is an amine acceptor. Thus, simple deglycosylation generates two BTG-reactive glutamine residues per antibody (one per heavy chain, at Q295), while an antibody with an N297Q substitution will have four BTG-reactive glutamine residues (two per heavy chain, at positions Q295 and Q297).

Disclosures relating to the transglutaminase-mediated preparation of ADCs include: Dennler et al. 2014, Innate Pharma 2013, Jeger et al. 2010, Pons et al. 2013, and Strop et al., 2013.

In particular, Pons et al. 2013 disclose the modification of an antibody with a four-amino acid glutamine-containing tag, which can be located at the C-terminus of one of its chains, to make it transglutaminase-reactive. (Attachment of tags or extensions to the C-terminus of an antibody chain in other contexts has also been disclosed. See, e.g., Liu et al. 2014.)

Other transglutaminase disclosures, more generally relating to the labeling or modification of proteins (including antibodies), include: Bregeon 2014, Bregeon et al. 2013 and 2014, Chen et al. 2005, Fischer et al. 2014, Kamiya et al. 2011, Lin et al. 2006, Mero et al. 2009, Mindt et al. 2008, Sato 2002, Sato et al. 2001, and Sugimura et al. 2007.

Full citations for the documents cited herein by first author or inventor and year are listed at the end of this specification.

SUMMARY OF THE INVENTION

In one embodiment, this invention provides a full-length antibody that has been modified to introduce glutamine residues that are substrates for transglutaminase, especially for BTG, by modifying the C-terminus of at least one of its heavy chains by adding thereto an extension containing at least one glutamine that is a substrate for transglutaminase. The extension has an amino acid sequence comprising EEQYASTY (SEQ ID NO:1), EEQYQSTY (SEQ ID NO:2), EEQYNSTY (SEQ ID NO:3), EEQYQS (amino acids 1 through 6 of SEQ ID NO:2), EEQYQST (amino acids 1 through 7 of SEQ ID NO: 2), EQYQSTY (amino acids 2 through 8 of SEQ ID NO:2), QYQS (amino acids 3 through 6 of SEQ ID NO: 6), or QYQSTY (amino acids 3 through 8 of SEQ ID NO: 2).

Preferably, the extension has an amino acid sequence comprising EEQYASTY (SEQ ID NO:1), EEQYQSTY (SEQ ID NO:2), or EEQYNSTY (SEQ ID NO:3).

We have also discovered that trimmed or truncated variants of some C-terminal extensions are also glutamine-reactive. Such trimmed variants are exemplified by EEQYQS (amino acids 1 through 6 of SEQ ID NO:2), EEQYQST (amino acids 1 through 7 of SEQ ID NO: 2), EQYQSTY (amino acids 2 through 8 of SEQ ID NO:2), QYQS (amino acids 3 through 6 of SEQ ID NO: 6), or QYQSTY (amino acids 3 through 8 of SEQ ID NO: 2). It appears that the trimmed sequences need the serine present (amino acid 6 of SEQ ID NO:2) in order to be glutamine-reactive.

In another embodiment, there is provided a method of making an antibody-drug conjugate, comprising the steps of:
(a) providing a full length antibody, at least one of whose heavy chains has a C-terminal extension having an amino sequence comprising EEQYASTY (SEQ ID NO:1), EEQYQSTY (SEQ ID NO:2), or EEQYNSTY (SEQ ID NO:3);
(b) providing an amine donor of the formula

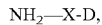

NH₂—X-D, wherein D represents a drug and X represents a bivalent linker group connecting drug D and the amine group NH₂,
(c) contacting the antibody and the amine donor in the presence of transglutaminase; and
(d) allowing the antibody and the amine donor to form the antibody drug conjugate by formation of an amide bond between a glutamine in the C-terminal extension and the amine group NH₂ of the amine donor moiety.

This invention further provides another method of making an antibody-drug conjugate, comprising the steps of:
(a) providing a full length antibody, wherein the antibody has been modified by adding to at least one of its heavy chains a C-terminal extension having an amino sequence comprising EEQYASTY (SEQ ID NO:1), EEQYQSTY (SEQ ID NO:2), or EEQYNSTY (SEQ ID NO:3);
(b) providing an amine donor of the formula

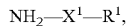

NH₂—X¹—R¹, wherein R¹ represents a first reactive functional group and X¹ represents a bivalent linker connecting reactive functional group R¹ and amine group NH₂;
(c) contacting the antibody and the amine donor in the presence of transglutaminase;
(d) allowing the antibody and the amine donor to form a modified antibody having attached thereto a first reactive functional group R¹, by formation of an amide bond between a glutamine in the C-terminal extension and the amine group NH₂ of the amine donor;
(e) contacting the modified antibody with a drug containing moiety of the formula

R²—X-D, wherein R² is a second reactive functional group that covalently reacts with the first reactive functional group R¹, D is a drug, and X is a bivalent linker connecting drug D and second reactive functional group R²; and
(f) allowing first and second reactive functional groups R¹ and R² to react to form the antibody-drug conjugate.

In another embodiment, this invention provides antibody-drug conjugate wherein the antibody is covalently linked to a drug moiety via an amide bond at the side chain of a glutamine residue in a C-terminal extension of a heavy chain of the antibody, the C-terminal extension having an amino sequence comprising EEQYASTY (SEQ ID NO:1), EEQYQSTY (SEQ ID NO:2), or EEQYNSTY (SEQ ID NO:3). Preferably, the antibody is an anti-CD70 or an anti-mesothelin antibody. Preferably, the drug moiety is a DNA minor groove binder (especially one that also alkylates the DNA upon binding) or a tubulysin analog.

BRIEF DESCRIPTION OF THE DRAWING(S)

Figure 1B:
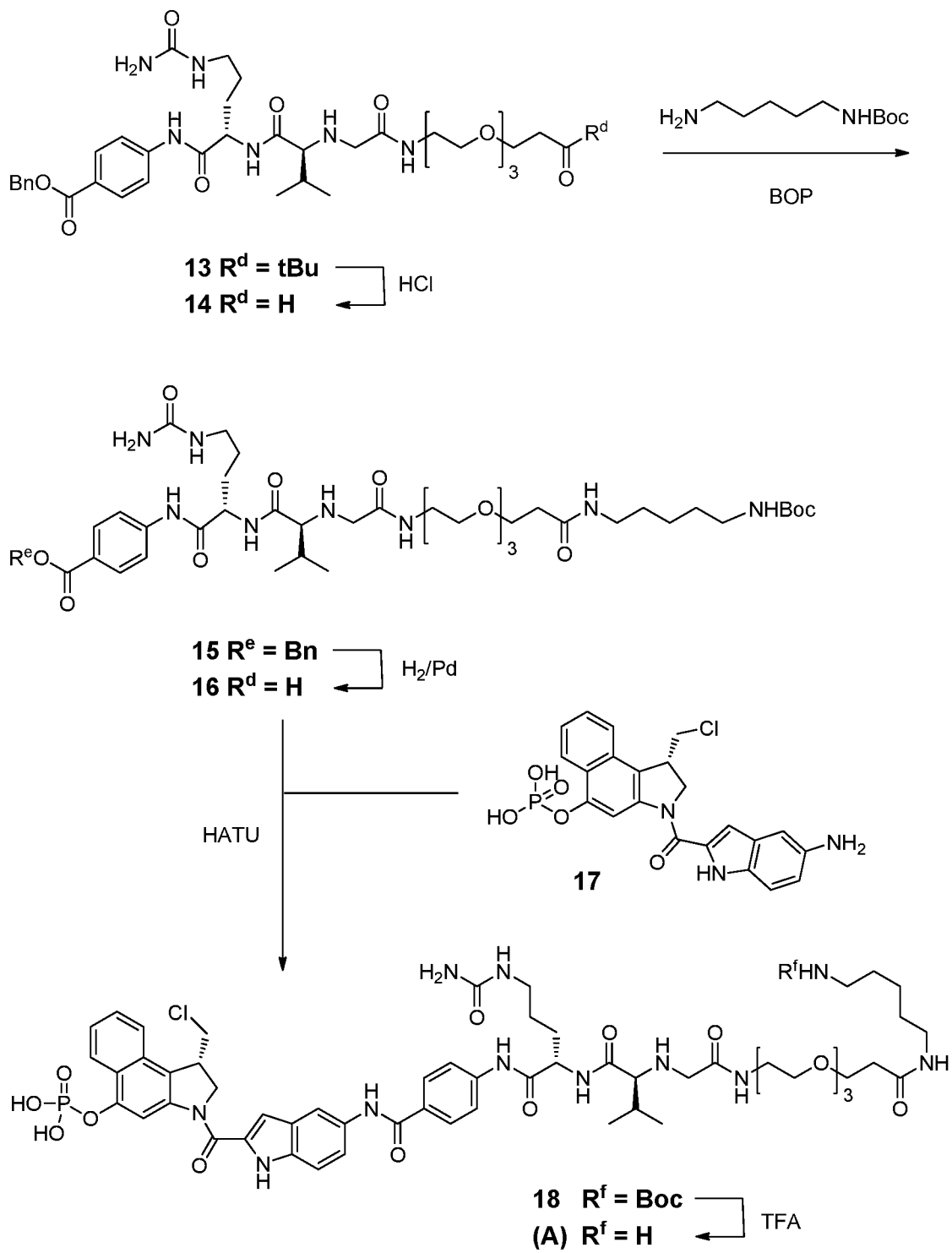
Figure 2:
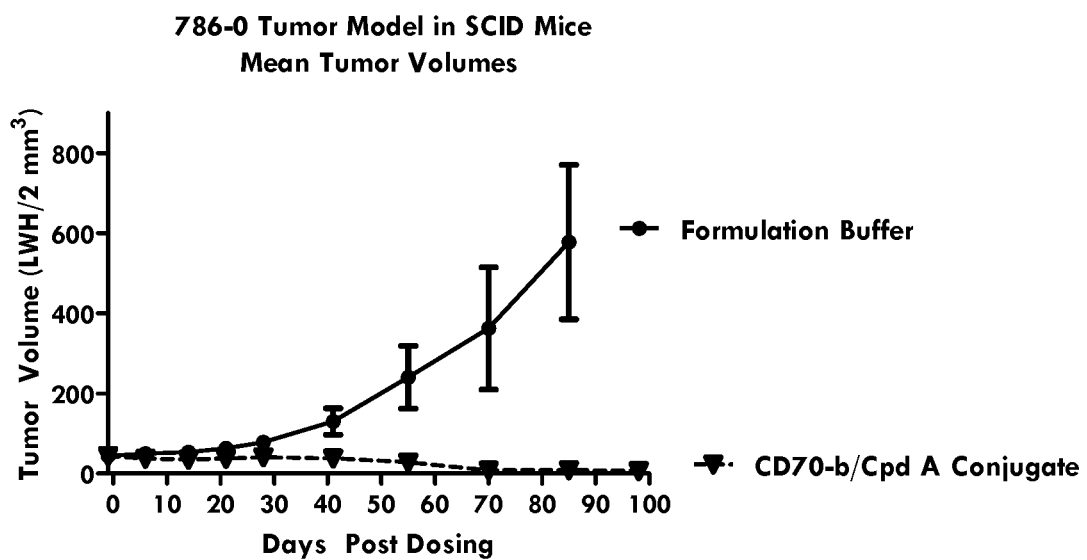
Figure 3:
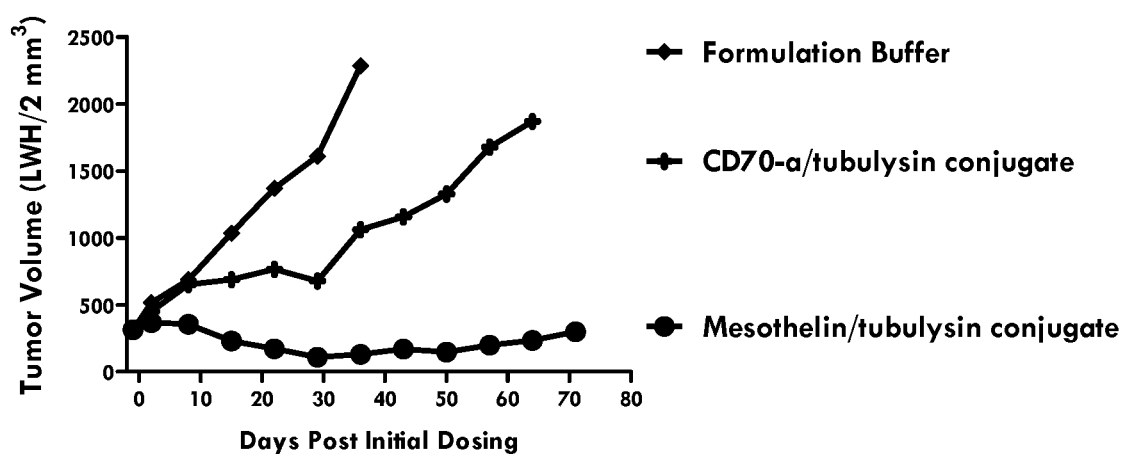
Figure 4:
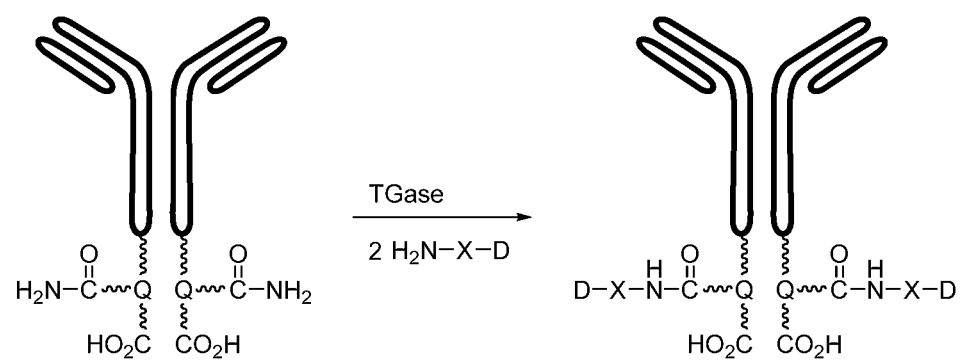
Figure 5:
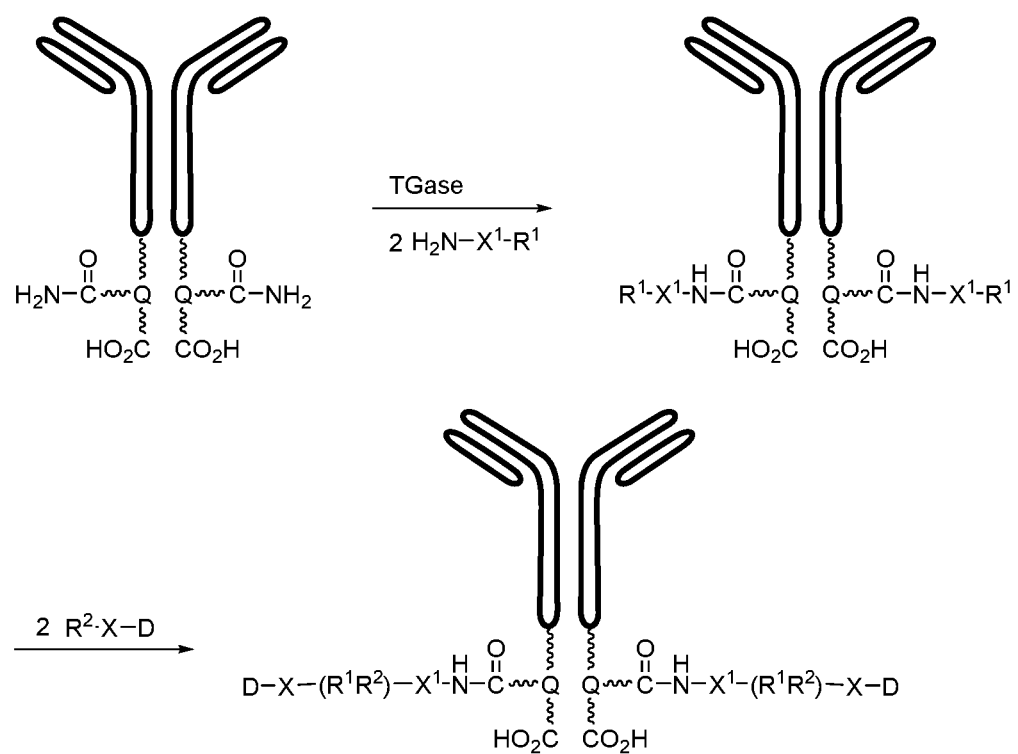

FIGS. 1a and 1b show, in combination, a scheme for the synthesis of amine donor (A).
FIG. 2 shows the activity of a conjugate, made by the one-step conjugation process.
FIG. 3 compares the activities of two conjugates made by the two-step conjugation process.
FIG. 4 and FIG. 5 depict the one-step and two-step conjugation processes, respectively.

DESCRIPTION OF EMBODIMENTS

Antibodies of the IgG1 isotype contain in their heavy chain constant region, at positions 297-300, the amino acid sequence EEQYNSTY (SEQ ID NO:3, numbering per EU as in Kabat). As discussed above, the glutamine residue Q295 is not a transglutaminase substrate unless the glycoside group normally attached at position 297 is absent, either by enzymatic removal or engineering a substitution of N297 to prevent formation of the N-linked glycoside bond.

We have discovered that if the sequence EEQYNSTY (SEQ ID NO:3) is appended to a heavy chain C-terminus of an antibody as an extension of thereof, the glutamine residue is a substrate for transglutaminase, making the antibody so modified amenable to transglutaminase-mediated conjugation. Further, we have discovered that variants of this sequence, EEQYASTY (SEQ ID NO:1) and EEQYQSTY (SEQ ID NO:2) are similarly effective. In the latter, both glutamine residues have been found to be transglutaminase-reactive.

The number of drug moieties attached to the antibody in an ADC is referred to as the drug-antibody ratio, or DAR. In the instance of an antibody where each heavy chain has a C-terminal extension having an amino acid sequence comprising EEQYASTY (SEQ ID NO:1) or EEQYNSTY (SEQ ID NO:3), the theoretical maximum DAR is 2, with one drug moiety attached to each heavy chain. In the instance of an antibody where each heavy chain has a C-terminal extension having an amino acid sequence comprising EEQYQSTY (SEQ ID NO:2), the theoretical DAR is 4, with one drug moiety attached to each glutamine residue in each of the extensions. Those skilled in the art will appreciate that the conjugation reaction is not always 100% efficient, and that a lesser number may be obtained for a given ADC preparation, for example a measured DAR of 1.7 where the theoretical maximum is 2, or a measured DAR of 3.5 where the theoretical maximum is 4.

Preferably, the antibody used in this invention is a full length antibody having two identical heavy chains and two identical light chains (kappa or lambda). Preferably, both heavy chains have a C-terminal extension according to this invention. Preferably, the antibody is of the IgG1 isotype. More preferably, the antibody has a heavy chain constant region that is an IgG1 variant having an amino acid sequence according to SEQ ID NO:4. This variant is of the R214/E356/M358 allotype and optionally has the C-terminal K447 clipped off post-translationally (numbering per EU as in Kabat). The antibody preferably is a monoclonal antibody, more preferably a human monoclonal antibody.

We have found that when the antibody has a C-terminal lysine, such as occurs in native antibodies, the lysine may act as an amine donor and crosslink the antibody heavy chains. Thus, it may be desirable to excise the C-terminal lysine.

Also, when an antibody is produced recombinantly, some of the heavy chain C-terminal chain lysine residues (amino acid 447 in FIG. 2) are often removed during the expression or purification steps by enzymes from the production host cell, leading to a heterogeneous product (both lysines present, one lysine removed, or both lysines removed). This heterogeneity is undesirable. To obtain a more heterogeneous product, both lysines can be intentionally removed, either by further enzymatic treatment of the initial product or by eliminating the codon for the C-terminal lysine from the nucleotide sequence used for recombinant expression. McDonough et al. 1992. Variant antibodies with the cysteine substitutions disclosed herein lacking heavy chain C-terminal lysine residues are also within the scope of this invention. Variant antibodies in which both the C-terminal glycine and lysine have been removed are also known and are included in the scope of this invention.

A preferred transglutaminase for use in this invention is BTG from *Streptomyces mobaraensis*, which is available commercially or can be prepared recombinantly.

C-Terminal extension bearing antibodies of this invention can be conjugated by a one-step or two-step process.

Schematically, one-step conjugation can be represented as shown in FIG. 4, using, by way of illustration and not of limitation, an antibody with C-terminal extensions having one glutamine (i.e., according to SEQ ID NO:1 or NO:3).

The amine donor can be represented by the formula (I)

$$H_2N-X-D \tag{1}$$

where D is a drug and X is a bivalent linker connecting drug D and the transglutaminase-reactive amine group $H_2N$.

Linker X can comprise alkylene chains and poly(ethylene glycol) chains alone or in combinations, as illustrated below:

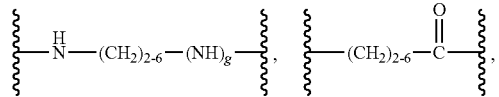

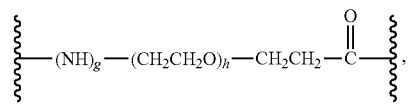

and combinations thereof, where the subscript g is 0 or 1 and the subscript h is 1 to 24, preferably 2 to 4. These segments can be combined, such as illustrated below:

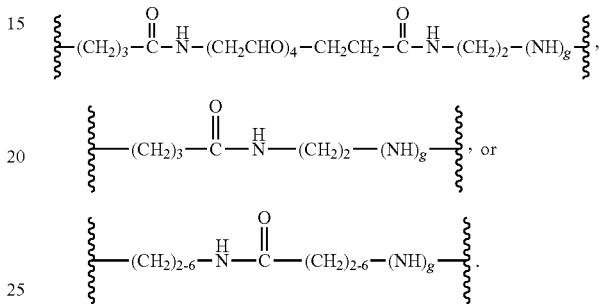

The linker X can also contain a cleavable group, for release of drug D from the conjugate after reaching the target site. Examples of cleavable groups include disulfides (cleavage by disulfide exchange), hydrazones (cleavage at low pH), and peptides (enzymatic cleavage). Alternatively, if no cleavable group is present, release of drug D from the conjugate can occur through catabolism of the antibody.

Also, linker X can contain a self-immolating group, as further described hereinbelow.

Preferred embodiments of the amine donor moiety (I), having a cleavable peptide, are represented by formulae (Ia) through (Ic):

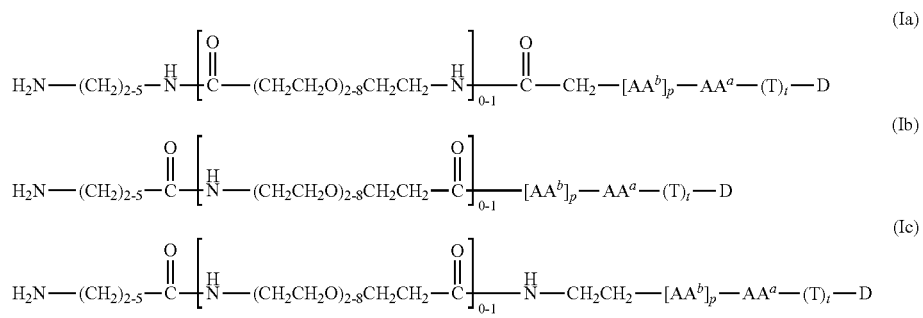

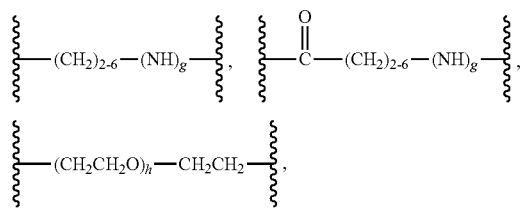

wherein

D is a drug;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

T is a self-immolating group; and t is 0 or 1.

In formulae (Ia), (Ib). and (Ic), -AA$^a$-[AA$^b$]$_p$-represents a polypeptide whose length is determined by the value of p (dipeptide if p is 1, tetrapeptide if p is 3, etc.). AA$^a$ is at the carboxy terminus of the polypeptide. Conversely, the last AA$^b$ is at the amino terminus of the polypeptide. Preferred polypeptides -AA$^a$-[AA$^b$]$_p$- are Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in H$_2$N-Val-Cit-CO$_2$H). More preferably, the polypeptide is Val-Cit, Val-Lys, or Val-Ala. Preferably, a polypeptide -AA$^a$-[AA$^b$]$_p$- is cleavable by an enzyme found inside the target (cancer) cell, for example a cathepsin and especially cathepsin B.

As indicated by the subscript t equals 0 or 1, a self-immolating group T is optionally present in amine donors (Ia), (Ib), and (Ic). When present, a self-immolating group provides spatial separation between drug D and the polypeptide, to avoid drug D sterically interfering with an enzyme's cleavage of the polypeptide to release the drug. The self-immolating group T preferably is a p-aminobenzyl oxycarbonyl (PABC) group, whose structure is shown below, with an asterisk (*) denoting the end of the PABC bonded to an amine nitrogen of drug D and a wavy line (∼∼∼) denoting the end bonded to the polypeptide -AA$^a$-[AA$^b$]$_p$-.

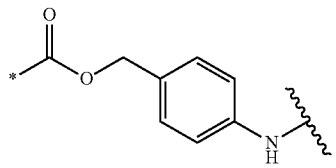 [SMILES: *Nc1ccc(COC(*)=O)cc1]

Schematically, the two-step process can be represented as shown in FIG. 5, using again by way of illustration and not limitation an antibody having C-terminal extensions having one glutamine each.

In this scheme, X$^1$ and X are linkers, D is the drug moiety, and R$^1$ and R$^2$ are complementary reactive functional groups that react covalently with each other to form (R$^1$R$^2$), completing the formation of the ADC. Components of linker X have been described above in the context of the one-step process. Linker X$^1$ can comprise alkylene and poly(ethylene glycol) chains, as described hereinabove for linker X.

Examples of pairings of reactive functional groups R$^1$ and R$^2$ and their reaction product (R$^1$R$^2$) are shown in Table I following.

TABLE I

Groups R$^1$ and R$^2$ and Their Reaction Product

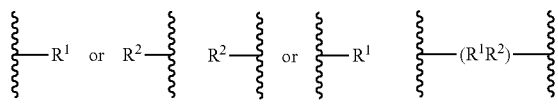

TABLE I-continued

Groups R$^1$ and R$^2$ and Their Reaction Product

Thus, the following pairings of reactive functional groups R$^1$ and R$^2$ are contemplated under Table I:

(a) first reactive functional group R$^1$ is an azide group and second reactive functional group R$^2$ is a dibenzocyclooctyne group;

(b) first reactive functional group R$^1$ is a dibenzocyclooctyne group and second reactive functional group R$^2$ is an azide group;

(c) first reactive functional group R$^1$ is a maleimide group and second reactive functional group R$^2$ is a thiol group;

(d) first reactive functional group R$^1$ is a maleimide group and second reactive functional group R$^2$ is a thiol group;

(e) first reactive functional group R$^1$ is a ketone group and second reactive functional group R$^2$ is a hydroxylamine group; and (f) first reactive functional group R$^1$ is a ketone group and second reactive functional group R$^2$ is a hydroxylamine group.

As ADCs are typically used in cancer treatment, the drug preferably is a cytotoxic drug that causes death of the targeted cancer cell. Cytotoxic drugs that can be used in ADCs include the following types of compounds and their analogs and derivatives:

(a) enediynes such as calicheamicin (see, e.g., Lee et al., J. Am. Chem. Soc. 1987, 109, 3464 and 3466) and uncialamycin (see, e.g., Davies et al., WO 2007/038868 A2 (2007) and Chowdari et al., U.S. Pat. No. 8,709,431 B2 (2012));

(b) tubulysins (see, e.g., Domling et al., U.S. Pat. No. 7,778,814 B2 (2010); Cheng et al., U.S. Pat. No. 8,394,922 B2 (2013); and Cong et al., US 2014/0227295 A1 (2014);

(c) DNA minor groove binder/alkylators, such as CC-1065 and duocarmycin (see, e.g., Boger, U.S. Pat. No. 6,5458,530 B1 (2003); Sufi et al., U.S. Pat. No. 8,461,117 B2 (2013); and Zhang et al., US 2012/0301490 A1 (2012));

(d) epothilones (see, e.g., Vite et al., US 2007/0275904 A1 (2007) and US RE42930 E (2011));
(e) auristatins (see, e.g., Senter et al., U.S. Pat. No. 6,844,869 B2 (2005) and Doronina et al., U.S. Pat. No. 7,498,298 B2 (2009));
(f) pyrrolobezodiazepine (PBD) dimers (see, e.g., Howard et al., US 2013/0059800 A1 (2013); US 2013/0028919 A1 (2013); and WO 2013/041606 A1 (2013)); and
(g) maytansinoids such as DM1 and DM4 (see, e.g., Chari et al., U.S. Pat. No. 5,208,020 (1993) and Amphlett et al., U.S. Pat. No. 7,374,762 B2 (2008)).

Thus, drug moiety D can be an enediyne, a tubulysin, a DNA minor groove binder/alkylator, an epothilone, an auristatin, a pyrrolobenzodiazepine, or a maytansinoid, or an analog or derivative thereof. A preferred drug moiety D is a DNA minor groove binder/alkylator.

An exemplary amine donor designed to be used in a one-step conjugation process is shown below:

(A)

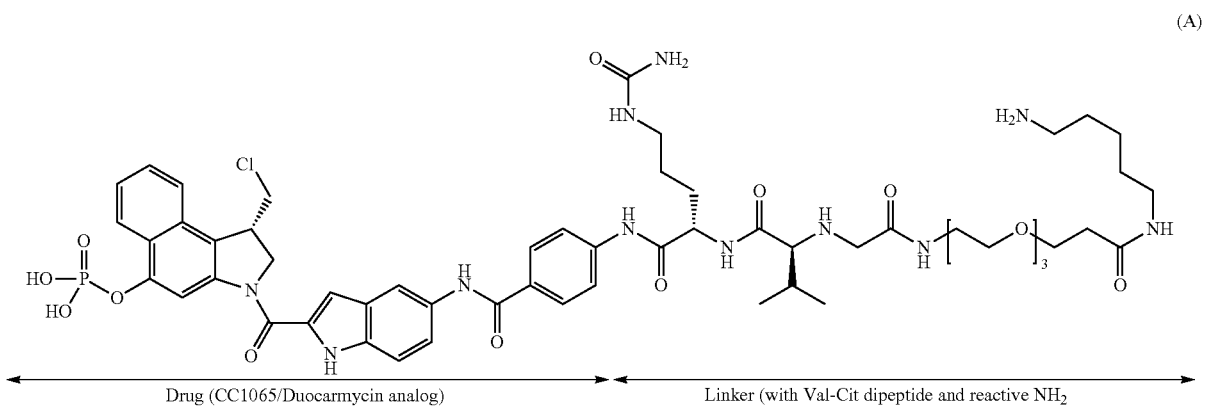

Drug (CC1065/Duocarmycin analog)      Linker (with Val-Cit dipeptide and reactive NH$_2$ In compound (A) the drug is a CC-1065/duocarmycin analog, which binds to the minor groove of DNA and then alkylates the DNA. The linker contains a valine-citrulline (Val-Cit) dipeptide, which is a substrate for the lysosomal enzyme cathepsin B, enabling cleavage of the linker to release the drug from the ADC.

The practice of this invention can be further understood by reference to the following examples, which are provided by way of illustration and not of limitation.

Example 1—Antibodies with C-Terminal Extensions

An expression vector for the heavy chain of anti-CD70 antibody 1F4 (Coccia et al. 2010) was modified by replacing the original nucleotide sequence encoding the heavy chain constant region with a modified one including an EEQYAS-TYR C-terminal extension (SEQ ID NO:5). The expression vector so modified was co-transfected along with an expression vector for the 1F4 light (kappa) chain into CHO-S cells. Stable clones were selected for the production of antibody 1F4 having a heavy chain constant region according to SEQ ID NO:6, which in turn lead to antibody 1F4 having an EEQYASTY (SEQ ID NO:1) C-terminal extension after the terminal arginine was clipped off post-translationally ("anti-CD70-a")

Analogously, the nucleotide sequence of SEQ ID NO:7 was used to produce antibody 1F4 with a heavti-CD70y chain constant region according to SEQ ID NO:8, which lead to antibody 1F4 with an EEQYQSTY (SEQ ID NO:2) after post-translation clipping off of the terminal arginine ("anti-CD70-b").

Anti-mesothelin antibody 6A4 (Terrett et al. 2012) having either an EEQYASTY (SEQ ID NO:1) or EEQYQSTY (SEQ ID NO:2) heavy chain C-terminal extension was similarly prepared, mutatis mutandis.

Example 2—Transglutaminase Mediated Conjugation

Representative procedures for conjugation by the one-step and two-step methods are described below.

Method 1 (One-Step Process):

The antibody, at ~2 mg/ml, in 50 mM Tris-HCl, pH 8.0, was reacted with 10-fold molar per site excess of the amine donor in the presence of 3 Units of recombinant bacterial transglutaminase per mg of antibody. The reaction was allowed to proceed for 5 h at 37° C. with continuous gentle mixing.

The conjugate was 0.2 μm filtered prior to Cation-exchange chromatographic purification. The SP Sepharose High Performance Cation Exchange column (CEX) was regenerated with 5 CV (column volume) of 50 mM HEPES, 5 mM Glycine, 1M NaCl, pH 5.5 (Buffer B). Following regeneration, the column was equilibrated with 3 CVs of equilibration buffer, 50 mM HEPES, 5 mM Glycine, pH 5.5 (Buffer A). The conjugate was loaded and the column was washed once with the equilibration buffer. The conjugate was eluted with a linear gradient from 0-100% B over 6 CV. The eluate was collected in fractions and analyzed by SDS-PAGE and Western analysis.

Method 2 (Two-Step Process):

The C-terminal extension bearing antibody, at ~2 mg/ml, in PBS, pH 7.4, was reacted with 20-fold molar excess per transglutaminase-rective glutamine with O-(2-aminoethyl-O'-(2-azidoethyl)) pentaethylene glycol (Sigma Aldrich) in the presence of 3 Units of recombinant bacterial transglutaminase per mg of antibody, overnight at 37° C. with continuous gentle mixing.

The amino azido modified antibody (azido-mAb) was purified using a mAb Select SuRe column (GE Healthcare) and then loaded onto a column pre-equilibrated with 1×PBS, pH 8.0. The azido-mAb was eluted from the column with 25 mM glycine, 10 mM succinic acid, pH 5.0. The eluate was collected in fractions and analyzed by SDS-PAGE.

The purified azido-Mab was dialyzed into PBS, pH 7.4 and concentrated to 4 mg/mL. The azido-Mab was reacted with a drug-linker compound having a dibenzocyclooctyne (DIBO) group at a 5× molar excess per azide group. The reaction was carried out at ambient temperature for 4 h. The conjugate was 0.2 μm filtered and buffer exchanged into formulation buffer (6× Volume) (20 mg/ml Sorbitol, 10 mg/ml glycine, pH 5.0). The formulated bulk was filtered through a 0.2 μm PES filter into sterile tubes and stored at −80° C.

Those skilled in the art will appreciate that the two-step process was illustrated with azide and DIBO as the complementary reactive functional groups, but that other pairings of complementary reactive functional groups can be used, mutatis mutandis.

Example 3—Synthesis of Amine Donor (A)

Compound 3.

To a solution of 4-nitrobenzoic acid 1 (Aldrich, 2.36 g, 14.12 mmol) in acetonitrile (50 mL) was added potassium carbonate (1.952 g, 14.12 mmol) followed by (bromomethyl)benzene 2 (Aldrich, 1.848 mL, 15.53 mmol). After stirring at 60° C. overnight, the reaction was cooled to room temperature (RT) and concentrated to remove the acetonitrile. The resulting white solid was dissolved in 100 mL water and 50 mL of ethyl acetate. The organic layer was separated, washed with brine, dried over anhydrous sodium sulfate, and concentrated in vacuo. The residue was suspended in toluene (2×8 mL) and concentrated in vacuo to give crude benzyl 4-nitrobenzoate 3 (3, 3.86 g, 15.01 mmol, 106% yield) as a white solid. $^1$HNMR (CDCl$_3$) δ 8.26 (m, 4H), 7.44 (m, 5H), 5.42 (s, 2H).

Compound 4.

To a solution of benzyl 4-nitrobenzoate (3, 3.76 g, 14.62 mmol) in acetone (40 mL) at 0° C. was added zinc dust (4.78 g, 73.1 mmol) followed by a solution of ammonium chloride (7.82 g, 146 mmol) in water. After stirring at RT for 1 h, the reaction was filtered through CELITE™ filter medium and then concentrated in vacuo. The residue was suspended in ethyl acetate, washed with water followed by brine, dried over anhydrous sodium sulfate, and concentrated in vacuo. The residue was purified by flash chromatography using an Isco 80 g column eluting with 0-50% ethyl acetate/hexanes to give benzyl 4-aminobenzoate 4 (2.93 g, 12.89 mmol, 88 yield) as a white solid. $^1$HNMR (CDCl$_3$) δ 7.91 (d, 2H), 7.30-7.41 (m, 5H), 6.65 (d, 2H), 5.33 (s, 2H), 4.12 (s, 2H); MS (ESI) m/z 228 (M+H)$^+$.

Compound 6.

A 200 mL flask was charged with benzyl 4-aminobenzoate 4 (3.6 g, 15.84 mmol), (S)-2-((((9H-fluoren-9-yl)methoxy)carbonyl)amino)-5-ureidopentanoic acid 5 (ChemImpex, 5.25 g, 13.20 mmol), HOBt hydrate (Aldrich, 3.03 g, 19.80 mmol), and EDC (ACT, 3.54 g, 18.48 mmol). The flask was purged with nitrogen and dichloromethane (DCM, 20 mL) followed by DMF (5 mL) was added. Copper (II) chloride (Aldrich, 2.130 g, 15.84 mmol) was then added to give a homogeneous dark brown solution. After stirring at RT for 4 h, an additional shot of HOBt and EDC was added. Stirring was continued at RT overnight. The reaction mixture was concentrated in vacuo and the residue was split into two batches that were each purified by flash chromatography using an Isco 120 g column eluting with 0-10% methanol/DCM. The product thus obtained was dissolved in minimal THF, diluted with ethyl acetate, and washed with saturated aqueous sodium bicarbonate solution. The organic layer was dried over anhydrous sodium sulfate and concentrated in vacuo. The resulting solid was triturated with ethyl acetate to give compound 6 (3.34 g, 5.51 mmol, 41.7% yield) as a yellow solid. MS(ESI) m/z 607 (M+H)$^+$.

Compound 7.

To a solution of compound 6 (3.34 g, 5.51 mmol) in THF (20 mL) at RT was added piperidine (2.73 mL, 27.5 mmol). After stirring at RT for 60 min, the reaction mixture was concentrated in vacuo. The crude product was purified by flash chromatography using an Isco 80 g column eluting with 0-20% methanol/DCM to give compound 7 (2.24 g, 5.83 mmol, 106% yield) as a white solid. MS(ESI) m/z 385 (M+H)$^+$.

Compound 9.

A 50 mL flask was charged with compound 7 (268 mg, 0.697 mmol), compound 8 (TCI, 355 mg, 1.046 mmol), and EDC (ACT, 200 mg, 1.046 mmol). The flask was purged with nitrogen and DCM (5 mL) followed by DMF (1 mL) were added. After stirring at RT for 1 h, the reaction was complete and the reaction mixture had solidified. The reaction mixture was concentrated to remove DCM, diluted with ethyl acetate, and washed with saturated aqueous sodium bicarbonate solution, 10% aqueous lithium chloride solution, and then saturated aqueous sodium bicarbonate solution again. The organic layer was then filtered to give crude compound 9 (443 mg, 0.628 mmol, 90% yield) which had precipitated out as a white solid. MS(ESI) m/z 706 (M+H)$^+$.

Compound 10.

To a solution of compound 9 (0.44 g, 0.623 mmol) in THF (5 mL) at rt was added piperidine (Aldrich, 0.309 mL, 3.12 mmol). After stirring at RT for 60 min, the reaction mixture had solidified and another 5 mL of THF was added. After stirring at RT for an additional 2 h, the reaction was concentrated in vacuo. The residue was suspended in 10% methanol/DCM and filtered to give crude compound 10 (245 mg, 0.507 mmol, 81% yield). The filtrate was concentrated in vacuo and the residue was purified by flash chromatography using an Isco 40 g column eluting with 0-20% methanol/DCM to give compound 10 (64 mg, 0.132 mmol, 21% yield) as a white solid. $^1$HNMR (DMSO) δ 7.7-8.1 (m, 5H), 7.30-7.49 (m, 5H), 5.58 (s, 1H), 5.34 (s, 2H), 4.32 (t, 1H), 3.61 (s, 1H), 2.98 (m, 2H), 1.62-1.93 (m, 3H), 1.43 (m, 2H), 0.92 (dd, 6H); MS (ESI) m/z 484 (M+H)$^+$.

Compound 12.

To a solution of compound 11 (Aldrich, 1.5 g, 5.41 mmol) in DCM (20 mL) at 0° C. was added DIPEA (Aldrich, 1.889 mL, 10.82 mmol) and then 2-bromoacetyl chloride (Aldrich, 0.495 mL, 5.95 mmol). After stirring at 0° C. for 10 min, the cooling bath was removed and stirring continued at RT for 1 h. The reaction mixture was quenched with saturated aqueous sodium bicarbonate solution and extracted with DCM. The pooled organic extracts were dried over anhydrous sodium sulfate and concentrated in vacuo. The residue was purified by flash chromatography using an Isco 40 g column eluting with 0-70% ethyl acetate/hexanes to give compound 12 (1.15 g, 2.89 mmol, 53.4% yield) as an orange oil. $^1$HNMR (CDCl$_3$) 7.00 (b, 1H), 3.91 (s, 2H), 3.50-3.71 (m, 14H), 2.54 (t, 2H), 1.46 (s, 9H).

Compound 13.

A mixture of compound 10 (300 mg, 0.620 mmol), compound 12 (297 mg, 0.744 mmol), potassium iodide (Aldrich, 103 mg, 0.620 mmol), and DIPEA (Aldrich, 0.217 mL, 1.241 mmol) in DMF (3 mL) was stirred at 40° C. for 6 h. After cooling to RT, the reaction was diluted with ethyl acetate and washed successively with saturated aqueous sodium bicarbonate solution, 10% aqueous lithium chloride, and brine. The organic layer was dried over anhydrous sodium sulfate, filtered, and concentrated in vacuo. The residue was purified by flash chromatography using an Iscor 40 g column eluting with 0-10% methanol/DCM to give compound 13 (336 mg, 0.420 mmol, 67.6% yield) as a yellow oil. MS(ESI) m/z 801 (M+H)$^+$.

Compound 14.

To a solution of compound 13 (0.33 g, 0.412 mmol) in dioxane (5 mL) was added 4N HCl in dioxane (10 mL). After stirring at RT for 1 h, the reaction mixture was concentrated in vacuo to give crude compound 14 as a colorless viscous oil which was used directly without further purification. MS(ESI) m/z 745 (M+H)$^+$.

Compound 15.

A 50 mL flask was charged with compound 14 (307 mg, 0.412 mmol), tert-butyl (5-aminopentyl)carbamate (Chem-Impex, 100 mg, 0.494 mmol), and BOP (Chem-Impex, 237 mg, 0.536 mmol). The flask was purged with nitrogen and DMF (2 mL) and DIPEA (0.180 mL, 1.030 mmol) were added. After stirring at RT for 1 h, the reaction mixture was diluted with ethyl acetate, and washed successively with saturated aqueous sodium bicarbonate solution, 10% aqueous lithium chloride solution, and saturated aqueous sodium bicarbonate solution again. The organic layer was dried over anhydrous sodium sulfate, filtered, and concentrated in vacuo. The residue was purified by flash chromatography using an Isco 40 g column eluting with 0-10% methanol/DCM to give compound 15 (261 mg, 0.281 mmol, 68.2% yield) as a colorless foam. MS(ESI) m/z 929 (M+H)$^+$.

Compound 16.

A solution of compound 15 (261 mg, 0.281 mmol) and 10% Pd/C (Aldrich, 1.495 mg, 0.014 mmol) in MeOH (3 mL) was stirred under an atmosphere of hydrogen (balloon) for 2 h. The reaction vessel was flushed with nitrogen and CELITE™ filter medium was added. The mixture was filtered through a thin pad of CELITE™ filter medium and washed with methanol. The filtrate was concentrated and the crude product was purified by flash chromatography using an Isco 40 g column eluting with 0-20% methanol/DCM. The resulting oil was lyophilized from acetonitrile/water to give compound 16 (206 mg, 0.238 mmol, 85% yield) as a white solid. $^1$HNMR (DMSO) δ 8.21 (t, 1H), 7.92 (d, 2H), 7.80 (t, 1H), 7.75 (d, 2H), 6.75 (t, 1H), 6.03 (t, 1H), 5.45 (s, 2H), 4.51 (t, 1H), 2.81-3.65 (m, 25H), 2.30 (t, 2H), 162-1.89 (m, 8H), 1.35 (s, 9H), 1.24 (t, 2H), 0.92 (dd, 6H); MS (ESI) m/z 839 (M+H)$^+$.

Compound 18.

To a solution of compound 16 (35 mg, 0.042 mmol), 2-(3H-[1,2,3]triazolo[4,5-b]pyridin-3-yl)-1,1,3,3-tetramethylsouroniumhexafluorophosphate (V) (HATU, Oakwood, 12.69 mg, 0.033 mmol) in DMF (1 mL), DIPEA was added to adjust the pH to above 8. The reaction mixture was stirred at RT for 15 min. To it, compound 17 (U.S. Pat. No. 8,852,599; 19.68 mg, 0.042 mmol) was added. Extra DIPEA was added to adjust the pH of reaction mixture above 8. The reaction mixture was stirred at RT for 30 min. HPLC analysis showed the reaction was complete. The reaction mixture was purified by preparative HPLC with 10-65% acetonitrile in water (with 0.1% TFA, 20 mL/min) on Phenomenex Gemini 5μ, C18 150×21.2 mm column. The fractions containing expected product were combined and freeze-dried to give compound 18 (21 mg, 0.016 mmol. 49.34%). MS(ESI) m/z 1292 (M+H)$^+$.

Amine Donor (A).

To a solution of compound 18 (21 mg) in DCM (1 mL), TFA (1 mL) was added. The reaction mixture was stirred at RT for 30 min, concentrated and purified by preparative HPLC with 10-65% acetonitrile in water (with 0.1% TFA, 20 mL/min) Phenomenex Gemini 5μ, C18 150×21.2 mm column. The fractions containing with expected product were combined and freeze-dried to give amine donor (A) (16 mg, 0.013 mmol, 81.3%), $^1$HNMR (DMSO) δ11.95 (s, 1H), 10.54 (s, 1H), 10.18 (s, 1H), 8.85 (s, 1H), 8.36 (s, 1H), 8.31 (s, 1H), 7.20-8.31 (m, 12H), 6.23 (s, 1H), 5.48 (s, 1H), 3.99-4.95 (m, 7H), 2.10-3.99 (m, 28H), 1.28-1.85 (m, 8H), 0.92 (dd, 6H); MS(ESI) m/z 1192 (M+H)$^+$.

Example 3—Activity of Conjugate Made by One-Step Process

FIG. 2 shows the activity of a conjugate made by the one-step conjugation process. The antibody was antibody CD70-b (see Example 1 above), having an EEQYQSTY (SEQ ID NO:2) C-terminal extension and the drug was amine donor (A) (see Example 3 above). The DAR was 3.9. Activity was tested against was 786-O cells, a human renal carcinoma cell line that expresses CD70, in a SCID mouse tumor model. As the traces show, the conjugate was effective in suppressing tumor growth.

Example 4—Activity of Conjugates Made by Two-Step Process

Antibody CD70-a (see Example 1 above), having an EEQYASTY (SEQ ID NO:1) C-terminal extension, was conjugated to a tubulysin analog as the drug, using a two step process. Suitable tubulysin analogs are described in Cheng et al., U.S. Pat. No. 8,394,922 B2 (2013); and Cong et al., US 2014/0227295 A1 (2014). The complementary pair of reactive functional groups were an azide as $R^1$ and a cyclooctyne as $R^2$. The DAR was 1.8.

Analogously, anti-mesothelin antibody 6A4 (Terrett et al. 2012) was modified with an EEQYASTY (SEQ ID NO:1) C-terminal extension and then conjugated to the same tubulysin analog by the two-step process, to yield a conjugate with a DAR of 1.6.

The efficacy of the two conjugates was tested against N87 cells, a gastric cancer cell line that expresses mesothelin but not CD70. The results are shown in FIG. 3. The CD70 conjugate was much less effective against N87 cells, as might have been expected because they do not express CD70.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Bregeon et al., US 2013/0189287 A1 (2013).
Bregeon, WO 2014/202773 A1 (2014).
Bregeon et al., WO 2014/202775 A1 (2014).
Chen et al., US 2005/0136491 A1 (2005).
Coccia et al., US 2010/0150950 A1 (2010).
Dennler et al., *Bioconjug. Chem.* 2014, 25, 569-578.
Fischer et al., WO 2014/072482 A1 (2014).
Fontana et al., *Adv. Drug Deliv. Rev.* 2008, 60, 13-18.
Innate Pharma, "A New Site Specific Antibody Conjugation Using Bacterial Transglutaminase," presentation at ADC Summit, San Fransisco, Calif., Oct. 15, 2013.
Jeger et al., *Angew. Chem. Int. Ed.* 2010, 49, 9995.
Kamiya et al., US 2011/0184147 A1 (2011).
Lin et al., *J. Am. Chem. Soc.* 2006, 128, 4542-4543.
Liu et al., U.S. Pat. No. 8,865,875 B2 (2014).
Mero et al., *Bioconjug. Chem.* 2009, 384-389.
Mindt et al., *Bioconjug. Chem.* 2008, 19, 271-278.
Pons et al., US 2013/0230543 A1 (2013).
Sato et al., U.S. Pat. No. 6,322,996 B1 (2001).
Sato, *Adv. Drug Deliv. Rev.* 2002, 54, 487-504.
Schibli et al., US 2007/0184537 A1 (2007).
Schrama et al., *Nature Rev. Drug Disc.* 2006, 5, 147.
Strop et al., *Chemistry & Biology* 2013, 20, 161-167.
Sugimura et al., *J. Biotechnol.* 2007, 131, 121-127.
Terrett et al., U.S. Pat. No. 8,268,970 B2 (2012).
Zhang et al., U.S. Pat. No. 8,852,599 B2 (2014).

SEQUENCE LISTING

Incorporated herein by reference in its entirety is a Sequence Listing named "SEQT_12452WOPCT.txt," comprising SEQ ID NO:1 through SEQ ID NO:8, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Feb. 25, 2015, and is approximately 20 KB in size.

The following Table II summarizes the descriptions of the sequences disclosed in this application.

TABLE II

| Sequence Summary | |
|---|---|
| SEQ ID NO: | SEQUENCE DESCRIPTION |
| 1 | Amino acid, C-terminal extension |
| 2 | Amino acid, C-terminal extension |
| 3 | Amino Acid, C-terminal extension |
| 4 | Amino acid, IgG1 variant |
| 5 | Nucleic acid, modified heavy chain constant region |
| 6 | Amino acid, modified heavy chain constant region |
| 7 | Nucleic acid, modified heavy chain constant region |
| 8 | Amino acid, modified heavy chain constant region |

What is claimed is:

1. A full length antibody, wherein at least one heavy chain has a C-terminal extension having an amino acid sequence consisting of EEQYASTY (SEQ ID NO:1) or EEQYQSTY (SEQ ID NO:2).

2. A full length antibody according to claim 1, wherein the C-terminal extension has an amino acid sequence consisting of EEQYASTY (SEQ ID NO:1).

3. A full length antibody according to claim 1, wherein the C-terminal extension has an amino acid sequence consisting of EEQYQSTY (SEQ ID NO:2).

4. An antibody-drug conjugate wherein the antibody is covalently linked to a drug moiety via an amide bond at the side chain of a glutamine residue in a C-terminal extension of a heavy chain of the antibody, the C-terminal extension having an amino acid sequence consisting of EEQYASTY (SEQ ID NO:1) or EEQYQSTY (SEQ ID NO:2).

5. An antibody-drug conjugate according to claim 4, wherein the C-terminal extension has an amino acid sequence consisting of EEQYASTY (SEQ ID NO:1).

6. An antibody-drug conjugate according to claim 4, wherein the C-terminal extension has an amino acid sequence consisting of EEQYQSTY (SEQ ID NO:2).

* * * * *